(12) United States Patent
Su et al.

(10) Patent No.: US 7,138,041 B2
(45) Date of Patent: Nov. 21, 2006

(54) ELECTROCHEMICAL BIOSENSOR BY SCREEN PRINTING AND METHOD OF FABRICATING SAME

(75) Inventors: Chein-Shyong Su, Hsintien (TW); Chia-Wei Chang, Hsintien (TW); Miao-Ling Hung, Panchiau (TW); Wen-Jing Cheng, Hsintien (TW); Tai-Guang Wu, Taipei (TW)

(73) Assignee: General Life Biotechnology Co., Ltd., Taipei (TW)

( * ) Notice: Subject to any disclaimer, the term of this patent is extended or adjusted under 35 U.S.C. 154(b) by 0 days.

(21) Appl. No.: 10/784,681

(22) Filed: Feb. 23, 2004

(65) Prior Publication Data

US 2005/0183953 A1   Aug. 25, 2005

(51) Int. Cl.
G01N 27/327 (2006.01)

(52) U.S. Cl. ............... 204/403.04; 204/403.01

(58) Field of Classification Search ...............
204/403.01–403.03, 403.1–403.12, 403.14,
204/409, 412; 205/777.5, 779, 792, 793.5
See application file for complete search history.

(56) References Cited

U.S. PATENT DOCUMENTS

| | | | |
|---|---|---|---|
| 5,120,420 A | 6/1992 | Nankai et al. | |
| 5,437,999 A | 8/1995 | Diebold et al. | |
| 5,565,085 A | 10/1996 | Ikeda et al. | |
| 5,658,443 A | 8/1997 | Yamamoto et al. | |
| 5,779,867 A | 7/1998 | Shieh | |
| 5,922,188 A | 7/1999 | Ikeda et al. | |
| 5,997,817 A | 12/1999 | Crismore et al. | |
| 6,129,823 A | 10/2000 | Hughes et al. | |
| 6,207,000 B1 | 3/2001 | Schwobel et al. | |
| 6,258,229 B1 | 7/2001 | Winarta et al. | |
| 6,258,254 B1 | 7/2001 | Miyamoto et al. | |
| 6,299,757 B1 | 10/2001 | Feldman et al. | |
| 6,309,526 B1 | 10/2001 | Fujiwara et al. | |
| 6,338,790 B1 | 1/2002 | Feldman et al. | |

(Continued)

OTHER PUBLICATIONS

Product Descriptions "Bayer Glucometer Elite XL", www.sugarcats.net/sites/harry/meter.html, dated Oct. 23, 2001.

*Primary Examiner*—Alex Noguerola
(74) *Attorney, Agent, or Firm*—Ladas and Parry LLP

(57) ABSTRACT

An electrochemical biosensor formed by screen printing and method of fabricating such biosensor is disclosed in the present invention. The biosensor can quickly absorb a sample to be measured therein, effectively control volume of the sample fed and "fill-and-position" the sample therein. The biosensor includes an electrode layer (electrode area) comprising two or three electrodes, which are a working electrode, a reference electrode and an auxiliary electrode (tri-electrode) on an insulating substrate. An active reaction layer containing reactant, reaction catalyst, mediator, wetting agent and surfactant is spread on the surface of the electrode layer. A sample inflow area is formed above the electrode area by adding an upper cover on top of a middle insulating layer with a U-shaped opening formed therein. Sample solution with a minute amount about 0.8 to 1 μl can be rapidly introduced into the electrode area and the active reaction layer via the inflow area by siphon or capillary, where the ingredient of the sample can be analysed by measuring reaction between the sample, reaction catalyst and mediator in the reaction layer using electrochemical potentiometric or amperometric method. An upwardly extended closed space formed within the upper cover above the electrode area adjacent to the front of conductive wires can be effectively used to control sample volume and "fill-and-position" the sample.

26 Claims, 3 Drawing Sheets

U.S. PATENT DOCUMENTS

| | | |
|---|---|---|
| 6,416,641 B1 | 7/2002 | Ikeda et al. |
| 6,488,828 B1 * | 12/2002 | Bhullar et al. ......... 204/403.01 |
| 6,547,954 B1 | 4/2003 | Ikeda et al. |
| 6,599,407 B1 | 7/2003 | Taniike et al. |
| 6,793,802 B1 * | 9/2004 | Lee et al. ................ 205/777.5 |
| 6,939,450 B1 * | 9/2005 | Karinka et al. ............. 204/409 |
| 2002/0003087 A1 * | 1/2002 | Chih-hui ..................... 204/400 |

* cited by examiner

ELECTROCHEMICAL BIOSENSOR BY SCREEN PRINTING AND METHOD OF FABRICATING SAME

BACKGROUND OF THE INVENTION

1. Field of the Invention

The present invention relates to an electrochemical biosensor formed by screen printing and a method of fabricating such biosensor.

2. Description of the Related Art

Recently, electrode sensors have been commercially utilized successfully for the fabrication of a variety of clinical measuring products, such as blood sugar, uric acid and cholesterol measuring devices, for their easy and low cost production processes and wide application of cheaper portable measuring devices. Taking the biggest and the most widely used blood sugar measuring device on market as an example, the leading manufacturers include Roche, Abbott, Bayer and Therasense and all of which fabricate blood sugar sensors by electrochemistry. The first generation of such sensors requires higher amount of blood sample (5–10 μl and above) and takes longer (30–60 seconds) to measure a sample. Hence, they are still not considered ideal although the amounts of blood sample and measuring time they require are much less than those conventional colorimetric method does. As technology has improved over the years, the latest generation of sensors only requires 0.3 μl (Freestyle by Therasense) or 1 μl (OneTouch Ultra by Lifescan), and measuring time has also been reduced to 5–10 seconds. Such sensors have become a guide for products of a similar kind and technological development, as well as for further research and development of different electrode structures.

U.S. Pat. No. 5,437,999 by Diebold et al in 1995 has disclosed a sensor including opposing working and counter electrode elements spatially displaced by a spacer having a cut-out portion forming a capillary space between the working and counter electrode elements and a vent port in the working or counter electrode where air can be vented. A precise minute amount of a sample can be introduced via the capillary space and brought into contact with electrodes and reagents. Such sensors can be fabricated by photolithography or screen printing but processes of affixing two insulating substrates with an electrode thereon are very complicated and expensive. U.S. Pat. No. 5,779,867 by Shieh in 1998 has also disclosed a glucose sensor generally comprising a sensor electrode, a reference electrode, and a corpuscle separation thin film carrier strip sandwiched therebetween, which can filter erythrocyte, and an opening where a sample can be introduced. The carrier strip can be used to control volume of the sample flowing into the carrier strip and to remove interruption of erythrocyte during reactions. However, the amount of the sample introduced and the speed of filtering cannot be effectively and efficiently controlled. U.S. Pat. No. 6,129,823 by Abbott has proposed an electrode strip in which electrodes are covered with one or more mesh layers. The improvement involves a partial occlusion of the mesh which underlays an aperture within an upper cover above the mesh, and the aperture is formed above or adjacent to a working electrode. The partial occlusion can reduce the total volume of blood required to perform a measurement. Such sensor only requires 2.0–2.5 μl of the sample but applies a mesh to reduce the volume of blood and distribute the sample. U.S. Pat. Nos. 6,299,757 and 6,338,790 by Therasense have also suggested two opposing working and counter electrodes with a highly hydrophilic thin film finely constructed therebetween, which can introduce a sample to a sample chamber. The volume of the sample can be strictly controlled down to 0.3 μl by the water hydrophilic thin film, which is the lowest in the field. However, the processes of fabricating such sensors are very complex and extremely costly. ROC (Taiwan) Patent Publication No. 268,095 by Shieh has disclosed the technique of electrode fabrication by screen printing, in which an electrically conductive film and insulating layer are produced by screen printing. A metal layer is formed by electroplating and a circular recess, containing a so-called bio layer, is formed by coating a working and a reference electrodes with insulating paste. Sample of about 10 μl can be dropped to the recess to be measured. Such technique requires a larger amount of sample and processing such sensors introduces numerous electroplating process steps. ROC (Taiwan) Patent No. 124,332 by Apex Biotechnology Corp. has disclosed an inflow area formed above an electrode area. Mesh containing surfactant is spread above the inflow and electrode areas and sample can be brought into the electrode area by capillary or siphon. Such application is similar to that developed by Abbott, which utilizes mesh for the inflow of sample and is thus more costly, is also restricted to the amount of sample required.

U.S. Pat. No. 6,258,229 by Winarta et al in 2001 has disclosed a disposable electrode strip, which claims to require less than 1 μl of liquid sample. A piece of gold/polyester or tin oxide/gold polyester film is cut to shape, forming a base layer of sensor. A $CO_2$ laser is used to score the gold or tin oxide/gold polyester film and the film is scored by the laser creating scoring line such that two electrodes at sample end and three contact points are formed at an electrical contact end. A piece of double-sided tape is cut to size and shape, forming middle layer with a U-shaped channel, which contains an electrode area. A top layer, which is placed and coextensive with the middle layer, has a vent opening, which forms a fluid sample channel between sample inlet and the middle of the vent opening, which enables the fluid channel to restrict the volume of fluid to less than 1 μl. Such design is similar to that disclosed in U.S. Pat. No. 5,120,420 by Nankai et al in 1992, except that electrodes are formed in a different way. The electrode sensor disclosed by Nankai et al is a bi-electrode sensor by screen printing an insulating board. A fluid channel is formed by transversely adhering two spacers on opposing ends of electrodes and a top layer without an opening on top of spacers, which in turn forms a channel transverse to a working electrode. By this way, the volume of sample flowing into the channel cannot be controlled and the sample is likely to float a vent opening, which causes contamination. Another improvement employed by Winarta et al, which applies a middle layer with a U-shaped opening on top of a working electrode and subsequently a top layer with a vent opening over the middle layer, forms a fluid sample channel between sample inlet and the middle of the vent opening. With this structure, sample fluid may float the vent opening when the size of which is too small. On the other hand, sample fluid will be retained at the edge of the vent opening when the size of which is appropriate. However, as the size of sensors is getting smaller, it is likely to touch the vent opening by hand which causes outflow of sample fluid and thus contamination.

From the above analysis, it is understood that in order to achieve smaller volume of sample fluid and faster analysis yet avoid any possible contamination, it is necessary to design electrodes which incorporate capillary and siphon.

SUMMARY OF THE INVENTION

It is an object of the present invention to provide a biosensor, which incorporates the above principle, and disclose an electrode area with rapid sample inflow and less volume with advantages such as simple structure, needing no mesh and no contamination due to outflow of sample fluid. According to the present invention, only 0.5–0.8 µl of sample is required and analysis can be completed in about 5–10 seconds.

According to the present invention, the biosensor is formed by screen printing and includes an electrode layer (electrode area) comprising two or three electrodes, which are a working electrode, a reference electrode and an auxiliary electrode (tri-electrode) on an insulating substrate. An active reaction layer containing reactant, reaction catalyst, mediator, wetting agent and surfactant is spread on the surface of the electrode layer. A sample inflow channel above the electrodes between an upper cover and a middle insulating layer is used to introduce sample solution into the electrode area and the active reaction layer by siphon or capillary. Ingredient of the sample can be analyzed by electrochemical potentiometric or amperometric method. Further, the present invention provides an upwardly extended close chamber formed within the upper cover above the electrode area adjacent to the front of conductive wires, which can be effectively used to control sample volume and "fill-and-position" the sample.

DESCRIPTIONS OF THE DRAWINGS

DETAILED DESCRIPTION OF THE INVENTION

Sensor

Figure 1:
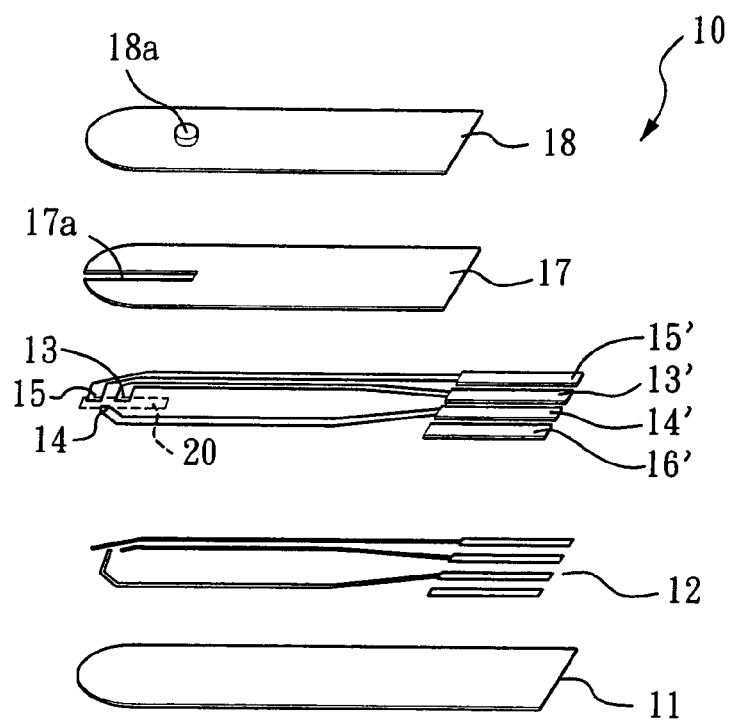
FIG. 1 is an exploded view illustrating the structure of an electrode sensor by screen printing according to the present invention with a slot.

According to the present invention, the structure of a tri-electrode biosensor 10 by screen printing illustrated in FIG. 1. Conductive wires 12 made of electrically conductive gel such as silver and gold, are formed on an insulating base plate or substrate 11 which is made of polyvinylcholorde (PVC), polyester (PE), polyether, polycarbonate, or the like, by screen printing. Electrode strips are then formed on top of the conductive wires 12 by printing another layer of electrically conductive material s such as carbon, gold, and platinum. Electrodes containing a working electrode 13, a reference electrode 14 and an auxiliary electrode 15 (no auxiliary electrode in a bi-electrode sensor) are disposed at one end above the layer of conductive wires 12. The corresponding contact ports 13', 14' and 15' at the other end with respect to the electrodes 13, 14, 15 can be connected to a measuring device (not shown) and a device activation line 16' can be automatically recognized by the measuring device. A non-electrically conductive or an insulating middle layer 17 which acts as an insulating dielectric layer as well as provides spacing is disposed above the 17a formed therein, is disposed above the insulating substrate insulating base plate 11 containing electrodes 13, 14, 15 by adhesion or screen printing. The insulating middle layer 17 has a Slot 17a designates a sample inflow channel. An upwardly extended closed chamber 18a with volume of about 2 µl, is formed within an upper cover 18 above and in communication with slot 17a at the rear end of slot 17a. An active reaction layer 20 containing substances of reactant, reaction catalyst (such as enzyme), mediator (such as dimethyl ferrocene, tetrathoiofulvalene), wetting agent (cellulose, hydroxyethyl cellulose, carboxymethyl cellulose, polyvinyl alcohol, polyvinyl, pyrrolidone and gelatine, etc.), and surfactant (Tween 20, triton X-100, surfynol, mega 8, etc.) is spread on the surface of the electrodes 13, 14, 15, which defines an electrode reaction area where reactions take place. When the upper cover 18 is adhered to the middle layer 17, the slot 17a defines a capillary inflow channel, which allows the sample such as blood to be rapidly introduced into and fill the electrode reaction area by capillary action upon contact with the front tip of the capillary inflow channel. Reactions induced by reaction catalyst can subsequently take place between reactant and mediator, in which electric current can be generated and measured by the measuring device. The inflow channel can provide the electrodes with rapid fill-in time (less than 1 second) and a minute amount of sample (less than 1 µl).

Figure 2:
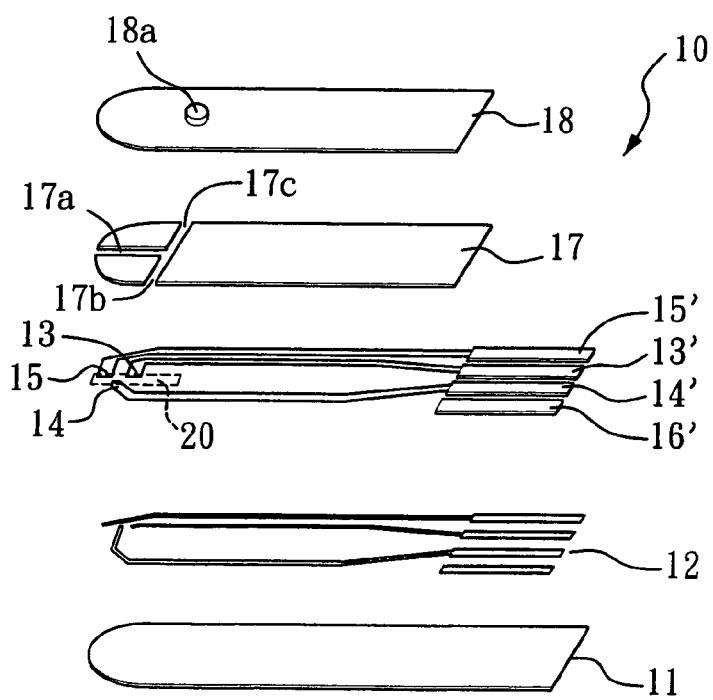
FIG. 2 is an exploded view illustrating the structure of an electrode sensor by screen printing according to the present invention with a T-shaped slot.

The structure of another electrochemical tri-electrode sensor 10 according to the present invention is illustrated in FIG. 2. Conductive wires 12 of electrically conductive materials such as silver, silver chloride, and gold, are formed on an insulating substrate 11, by screen printing. Electrodes of electrically conductive materials such as carbon, carbon, and platinum, comprising a working electrode 13, a reference electrode 14 and an auxiliary electrode 15 are printed on the conductive wires 12. The corresponding electrodes 13', 14' and 15' with respect to the electrodes 13, 14, 15 are contact ports to a measuring device (not shown in figure), whereas a device activation line U16 can be automatically recognized by the measuring device. A middle layer 17 of insulating material with a T-shaped slot 17a formed there, is formed on top of the insulating substrate 11 containing electrodes by adhesion or coating a layer of insulating paste by screen printing. An upper cover 18 containing an upwardly extending closed chamber 18a with volume of about 2 µl is formed on top of the middle layer 17 and the closed chamber 18a is positioned above the intersection of the T-shaped slot 17a. A sample inflow channeled is formed between the layer 17 and the upper cover 18 while 17b and 17c form air vents on opposite sides of the sensor 10. Sample such as blood can be rapidly introduced into and field an electrode reaction are 20 by capillary upon contact with the front tip of capillary inflow channel. Similar to FIG. 1, the sample is configured not to go beyond chamber 18a along the inflow channel. In addition, same venting effect can be achieved by removing either air vent 17b or 17c.

Insulating Substrate

Insulating substrate can be made of a variety of materials such as polymer, plastics, and ceramics. Materials should be chosen according to the requirement and application of electrode materials. For example, soft material should be chosen for invasive type sensors to reduce pain and avoid hurting tissues. For such sensors, insulating polymer materials such as polycarbonate, polyester, polyethylene terephthalate (PET), polyvinylchloride (PVC), polyether, polyamide, polyurethane, polyamide, etc., can be adapted. On the other hand, rigid materials which are not easy to be ruptured or bent, such as ceramics including silica or aluminum dioxide, can be adapted. With regard to measurement outside a human body, width of the insulating substrate is generally between 3 and 15 μm and more precisely between 5 and 10 μm. Thickness is between about 50 and 800 μm and more precisely between 200 and 400 μm. Length of the insulating substrate depends on different factors and may be between about 1 and 8 cm and more precisely between 2 and 5 cm.

Layer of Electrically Conductive Wires and Electrodes

As illustrated in FIG. 1, a layer of electrically conductive wires 12 made of electrically conductive materials such as silver, gold and platinum, is formed by screen printing, which is for connecting electrodes and a measuring device. Materials with high electrical conductivity and low resistance can reduce impedance of the electrodes and therefore increase signals of detected current. Electrically conductive material such as carbon paste can be printed on top of the wires 12 and a device activation line 16 can be automatically recognized by the measuring device. Apart from a reference electrode 14, wires 12 are completely coated. The exposed surface of silver wire in electrode 14 can be processed electrochemically to form a reference electrode of silver chloride, or processed electrochemically to form a reference electrode of silver chloride, or printed by silver/silver chloride ink. In the latter case, silver chloride processing is not necessary.

Middle Insulating Layer

Middle insulating layer 17 can be formed by printing or adhering dielectric material above electrodes, which in turn covers the carbon surface not required to be exposed and provides a reaction region with fixed area.

Reaction Reagents Area

Reaction reagents are spread on top of electrodes, which include reaction catalyst, buffer solution, binder, mediator, surfactant, etc. For example, when glucose is measured, the catalyst can be glucose oxidase or dehydrogenase. The ingredient of binder contains polymer or wetting agent including cellulose, polyvinyl alcohol, gelatine, surfactant, etc., such as Tween-20, Triton X-100, Surfynol, and Mega 8, which can dissolve and disperse sample and reagents and provide hydrophile and dispersion for capillary inflow channel. Therefore, the reaction reagent layer can provide both reaction and capillary, which not only fills sample in electrodes for analysis of reactions, but also provides electric current generated by reactions in electrodes for quantitative analysis of the sample. Preferred mediator, depending on requirement of different measurements, should have redox potential between −100 and +500 mV. Fore example, ferrocene such as dimethylferrocene, tetrathiafulvalene and derivative or complex of both can be applied. A lower potential can avoid interfering materials in the sample, while higher electron conducting efficiency can provide stronger electric current signals. Buffer solution can maintain pH within a fixed range, generally between 4 and 9 and preferably between 5 and 8. Useable buffer solutions include phosphoric salt, acetate salt, citrate salt, etc., and concentration can rage between 10 and 1000 mmole/l and preferably between 30 and 1000 mmole/1.

Capillary Inflow Layer

Capillary inflow channel is formed by adding a middle layer 17 and an upper cover 18 on the top of electrodes 13, 14, 15, 17a represents a sample capillary channel and 17b and 17c, which can exist independently, are air vents on opposite site of a sensor shaped design). The volume of the inflow channel can be adjusted by varying thickness of the middle layer 17 and width of channel 17a. The thickness of the inflow channel is generally between 20 and 400 μm and preferably between 50 and 200 μm. The length of the hollow inflow channel is between 2 and 8 mm and the width of which is between 0.5 and 5 mm and preferably between 1 and 2 mm. The volume of the hollow inflow channel is between 0.05 and 16 μl and a volume between about 0.5 and 4 μl is required when actual measurement is performed. The time between a sample being in contact with the edge of the inflow channel and filling-in the inflow channel is less than 1 second.

Figure 3:
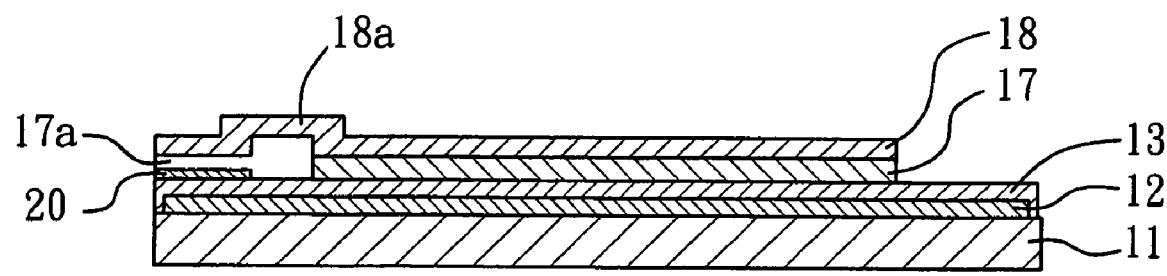
FIG. 3 is a longitudinal, cross-sectional view of the electrode sensor by screen printing according to the present invention.
Figure 4:
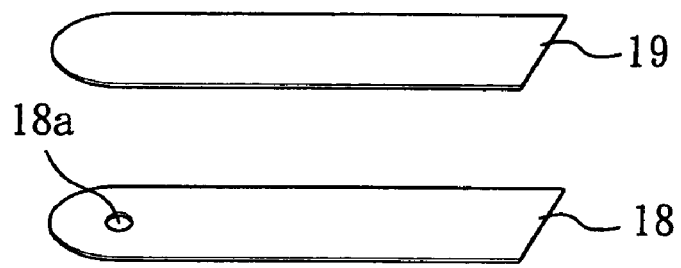
FIG. 4 is an exploded view illustrating the structure of an upper cover with an upwardly extended closed chamber formed therein according to the present invention.
Figure 5:
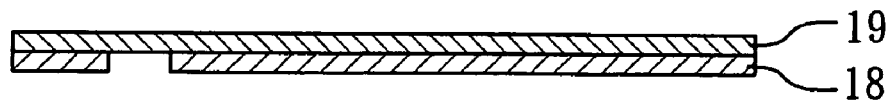
FIG. 5 is a longitudinal, cross-sectional view of the structure of the upper cover with an upwardly extended closed chamber formed therein according to the present invention.
Figure 6:
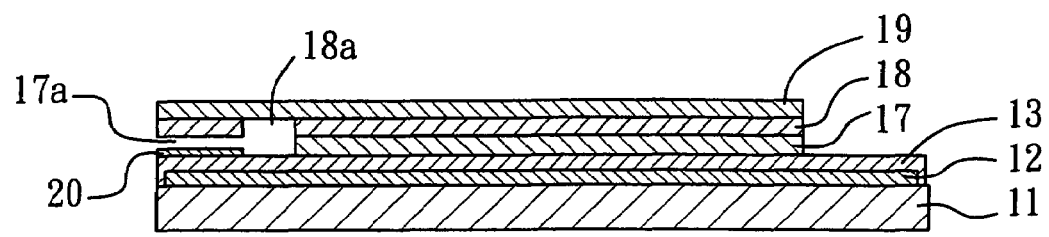
FIG. 6 is a longitudinal, cross-sectional view of the structure of an electrode sensor with an upwardly extended closed chamber formed therein.

The chamber 18a, in the upper cover 8 can be round, rectangular or of other geometry shape and the desired size can be between 0.5 and 4 mm. The location of an opening of the chamber 18a is above a rear end of the inflow channel and behind a working electrode. Blood sample can be filled in the reaction area, which the flowing of the sample is then stopped by the opening of the chamber. The spacing layer 17 and the upper cover 18 can be made of transparent opaque insulating materials such as plastics or polymers including PVC, Mylar, etc. Chamber 18a may be transparent for better inspection visually of sample flowing in and protection of sensor. The upper cover can be formed by 2 steps. The first step is to form opening 18a in the upper cover, as shown in FIG. 1 and the second step is to apply another thin plate 19 (as shown in FIGS. 4 and 5). FIGS. 3 and 6 show the sensor illustrated in FIG. 1 in longitudinal, cross-sectional view, which contains the thin plate 19.

Filling Detecting Device

Filling detecting device is designed to detect if a sample is filled above three electrodes. For a tri-electrode type sensor, if working electrode is disposed at the outer edge of inflow channel, filling detection can be arranged by using working electrode and auxiliary electrode and by monitoring electric current, potential and impedance. Impedance between working and reference electrodes is infinite by potentionmetry when no sample is present and decreases significantly when sample is filled inside the inflow channel area, by which parameter of electrochemical analysis is activated when sample is filled. For a bi-electrode type sensor, similar method can be applied. In order to apply electrodes for filling detection, distribution of electrodes should be the same as direction of sample flow. That is, working electrode needs to be in contact with sample ahead of auxiliary electrode and subsequently compete filling of sample can be determined. Similarly auxiliary electrode can be arranged to be in contact with sample ahead of working electrode, and vice versa.

Electrochemical Analysis

When electrodes are assembled, sensors can be cut by die cutting or punching. Sample analysis can be performed by connecting the sensor to a palm electrochemical device. Analysis can be performed by varied methods, such as chronoamperometry (0–0.6 V), which measures stationary current, or total charge within fixed time at constant potential. The total amount of charge, which is integral of electric current and time, and stationary current are proportional to the concentration of sample. Measuring device can also incorporate filling detection in the sensor, where parameter of electrochemical analysis can be activated when the measuring device detects a signal of filling, which in turn can increase accuracy of measurement. Especially when the overall measuring time is less than 10 seconds, a tiny error in time may result in large difference.

The present invention will now be applied by way of taking blood sugar as examples. It is intended to demonstrate the preferred embodiments rather than to limit the scope of the present invention.

EXAMPLE 1

Fabrication of Glucose Sensor by Screen Printing

A layer of electrically conductive silver paste is formed on a polyporpylene synthetic substrate 11. by 300 mesh screen printing, which is dried and heated for 30 minutes at 50° C., and three electrodes (working electrode 13, reference electrode 14 and auxiliary electrode 15) are printed by carbon paste thereon. The substrate 11 is again heated for 15 minutes at 90° C. and printed by insulating gel, which is subsequently dried and hardened under ultraviolet light to form an insulating layer with an inflow reaction are 17c, 17b and 17c (for sensors with air vents). Reaction reagents of 2–6 μl, containing 0.5–3 units of glucose oxidase, 0.1–1% of polyvinyl alcohol, pH 4.0–9.0 and 10 14 mM potassium phosphate as buffer solution, 10–100 mN potassium chloride, 0.05–0.5% of dimethylferrocene, 0.005%–0.2% tween–20, 0.005%–0.2% of sufynol and 011%–1.0% of carboxymethyl cellulose are spread on the recessed inflow channel area 17a. The substrate is dried at 45° C. for one hour and an upper cover 18 with an opening 18a formed therein is adhered on top of the substrate 11. A transparent upper cover 19 is pressed above the substrate 11 and sensors can be cut by die cutting from the substrate 11.

EXAMPLE 2

Standard Glucose Solution and Whole Blood Measurement

Standard potassium phosphate buffer solution (pH 7.4) is disposed containing glucose with a concentration of 0–400 mg/dl. The sample solution is measured by an electrochemical device (CHInstrument Co. 650A) in conjunction with a sensor according to Example 1 under a measuring potential of 100 mV for 8 seconds. The volume of sample solution is 3 μl for every measurement and the volume of sample solution introduced into the sensor for every measurement is less than 3 μl. The measuring results are listed in Table 1:

TABLE 1

Results of standard glucose measurements

| Glucose Concentration (mg/dl) | Charge (μ coulomb) |
|---|---|
| 0 | 0.690 |
| 25 | 1.532 |
| 50 | 2.952 |
| 100 | 5.248 |
| 200 | 7.400 |
| 400 | 9.577 |

Whole blood sample can also be measured by sensors according to the present invention. Table 2 shows results of by measuring fresh vain whole blood sample with glucose additive with a measuring potential of 100 mV and volume of 2 μl.

TABLE 2

Results of whole blood measurements with varied glucose addition

| Glucose Concentration (mg/dl) | Charge (μ coulomb) |
|---|---|
| 80 | 1.556 |
| 105 | 2.636 |
| 130 | 3.440 |
| 180 | 5.946 |
| 280 | 9.707 |
| 380 | 11.733 |
| 480 | 12.464 |
| 580 | 13.945 |

EXAMPLE 3

Measurements of Blood Sugar with Varied Volume of Whole Blood

Electrode sensors according to Example 1 are employed, which provide whole blood samples with different volume required in the present invention. Vein whole blood samples are mixed with standard glucose solution, which in turn form solutions with a concentration of 300 mg/dl.

Figure 7:
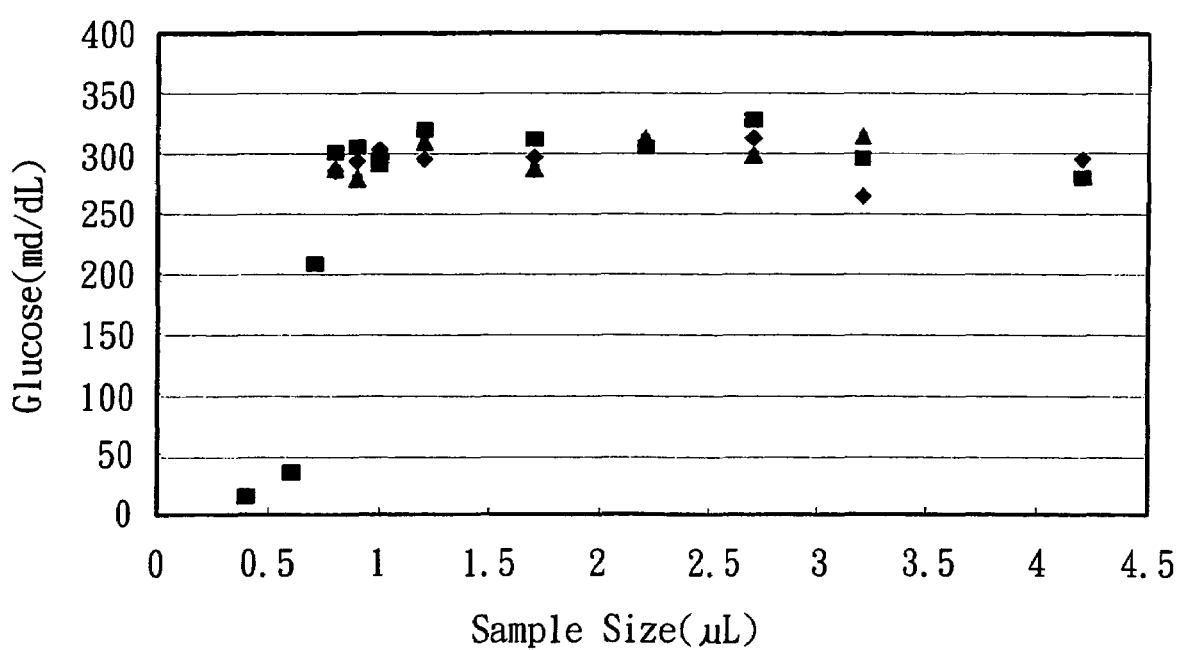
FIG. 7 shows the influence of whole blood volume on measurements.

The method of measurements is to provide whole blood samples with different volume and supply samples by siphon under conditions set out in Example 2. As shown in FIG. 7, when the volume of a sample is insufficient (e.g., of less than 0.5 1), the concentration of glucose is low. Conversely, when the volume of a sample is above 0.8 1, the measured glucose concentration si near that in the sample solution, and the whole amount of the sample cannot be introduced into the sensor. That is, the more the volume of a sample is supplied, the more volume of the sample will be redundant, since inflow reaction channel is saturated with the sample and cannot accommodate more solution. The front edge of sample does not go beyond the intersection between 18a and the inflow channel, which is the evidence that the volume of sample solution can be effectively controlled and restricted.

What is claimed is:

1. An electrochemical biosensor, comprising:
an insulating substrate;
a layer of electrically conductive wires disposed on said insulating substrate;
an electrode layer comprising a plurality of electrodes including a reference electrode and at least one electrode, and at least two contact ports adapted to connect to a measuring device, said electrode layer being disposed on said layer of electrically conductive wires except for said reference electrode;
a middle insulating layer disposed on said electrode layers without covering said electrodes and said contact ports, said middle insulating layer having a slot therein, above said electrodes;
an active reaction layer having substances of reactant, reaction catalyst, mediator and surfactant spread on the surface of said electrodes and defining an electrode reaction area; and
an upper cover adhered to said middle insulating layer, said upper cover having a closed chamber therein disposed at a rear end of said slot and extending above and in communication with said rear end of said slot, said slot defining a capillary inflow channel to enable a sample to be rapidly introduced into and fill said electrode reaction area by capillary action upon contact with a front tip of said capillary inflow channel and flow of said sample is stopped at a certain point along said capillary inflow channel due to said chamber.

2. The electrochemical biosensor according to claim 1, wherein said biosensor is a bi-electrode system and said at least one electrode is a working electrode.

3. The electrochemical biosensor according to claim 1, wherein said biosensor is a tri-electrode system and said at least one electrode —includes a working electrode and an auxiliary electrode.

4. The electrochemical biosensor according to claim 3, wherein said sample can be detected when it is introduced above said working electrode and said auxiliary electrode.

5. The electrochemical biosensor according to claim 1, wherein said slot is T-shaped.

6. The electrochemical biosensor according to claim 5, wherein the length and width of said slot is between 2 and 8 mm and between 0.5 and 5 mm, respectively.

7. The electrochemical biosensor according to claim 1, wherein said insulating substrate is made of material selected from the group consisting of polycarbonate, polyester, polyether, nylon, polyurethane, polyimide, polyvinylchloride (PVC), glass, glass fiber plate, ceramics and polyethylene terephthalate (PET).

8. The electrochemical biosensor according to claim 1, wherein said layer of electrically conductive wires is made of silver.

9. The electrochemical biosensor according to claim 1, wherein said layer of electrically conductive wires is made of silver chloride.

10. The electrochemical biosensor according to claim 1, wherein said layer of electrically conductive wires is made of gold.

11. The electrochemical biosensor according to claim 1, wherein said electrode layer is made of carbon.

12. The electrochemical biosensor according to claim 1, wherein said electrode layer is made of silver.

13. The electrochemical biosensor according to claim 1, wherein said electrode layer is made of gold.

14. The electrochemical biosensor according to claim 1, wherein said electrode layer is made of platinum.

15. The electrochemical biosensor according to claim 1, wherein said reaction catalyst is a bio catalyst.

16. The electrochemical biosensor according to claim 15, wherein said bio catalyst is an enzyme.

17. The electrochemical biosensor according to claim 1, wherein the thickness of said middle insulating layer is between 20 and 400 µm.

18. The electrochemical biosensor according to claim 1, wherein the thickness of said middle insulating layer is between 50 and 200 µm.

19. The electrochemical biosensor according to claim 1, wherein the length and width of said slot is between 2 and 8 mm and between 0.5 and 5 mm, respectively.

20. The electrochemical biosensor according to claim 1, wherein the volume of said closed chamber is between 0.5 and 4 µm.

21. The electrochemical biosensor according to claim 1, wherein said biosensor contains a device activation line which can activate said measuring device automatically.

22. The electrochemical biosensor according to claim 1, further comprising a thin plate disposed on top of said upper cover.

23. A method of fabricating an electrochemical biosensor, comprising the steps of:

forming a layer of electrically conductive wires on a substrate by screen printing which then is dried between 40° C. and 120° C.;

forming an electrode layer on top of said layer of electrically conductive wires by screen printing and drying said substrate between 40° C. and 120° C.;

forming a middle insulating layer with a slot formed therein above said electrode layer, wherein a working electrode, a reference electrode and an auxiliary electrode are confined within said slot and the opposite ends of said electrodes are exposed to make contact with a measuring device;

applying an active reaction layer on said slot;

adhering an upper cover formed with an opening therein above said middle insulating layer, wherein said opening is positioned at a rear end of said slot; and applying a surface layer above said upper cover, wherein said opening defines a closed chamber within said upper cover above and in communication with said rear end of said slot, said slot defining a capillary inflow channel such that a sample of substance can be rapidly introduced into and fill said electrode layer by capillary action upon contact of the substance with a front tip of said capillary inflow channel, and flow of said sample in said slot is stopped at a certain point in said slot due to said chamber.

24. The method of claim 23, wherein said middle insulating layer is formed on top of said electrode layer by screen printing.

25. The method of claim 23, wherein said slot is a T-shaped slot and the transverse opening of said T-shaped slot forms two air vents on opposite sides of said biosensor.

26. The method of claim 23, wherein said middle insulating layer is formed on top of said electrode layer by adhesion.

* * * * *